US012569225B2

(12) United States Patent
Lu et al.

(10) Patent No.: US 12,569,225 B2
(45) Date of Patent: Mar. 10, 2026

(54) METHOD AND DEVICE FOR DETECTING TISSUE FIBROSIS

(71) Applicants:Wuxi Hisky Medical Technologies Co., Ltd., Jiangsu (CN); PEKING UNIVERSITY, Beijing (CN)

(72) Inventors: Fengmin Lu, Beijing (CN); Mingjie Yao, Beijing (CN); Leijie Wang, Beijing (CN); Jinhua Shao, Wuxi (CN); Jin Sun, Wuxi (CN); Houli Duan, Wuxi (CN)

(73) Assignees: Wuxi Hisky Medical Technologies Co., Ltd., Wuxi (CN); PEKING UNIVERSITY, Beijing (CN)

( * ) Notice: Subject to any disclaimer, the term of this patent is extended or adjusted under 35 U.S.C. 154(b) by 1214 days.

(21) Appl. No.: 16/932,207

(22) Filed: Jul. 17, 2020

(65) Prior Publication Data

US 2020/0345329 A1 Nov. 5, 2020

Related U.S. Application Data

(63) Continuation of application No. PCT/CN2019/072227, filed on Jan. 17, 2019.

(30) Foreign Application Priority Data

Jan. 19, 2018 (CN) .......................... 201810055510.7

(51) Int. Cl.
| | |
|---|---|
| *A61B 8/08* | (2006.01) |
| *A61B 8/00* | (2006.01) |

(52) U.S. Cl.
CPC ............ *A61B 8/485* (2013.01); *A61B 8/0833* (2013.01); *A61B 8/0858* (2013.01); *A61B 8/5223* (2013.01)

(58) Field of Classification Search
CPC ..... A61B 8/485; A61B 8/0833; A61B 8/0858; A61B 8/5223; A61B 8/085
See application file for complete search history.

(56) References Cited

U.S. PATENT DOCUMENTS

| | | | |
|---|---|---|---|
| 2011/0306849 A1* | 12/2011 | Cales | .................. A61B 5/4244 600/301 |
| 2011/0313276 A1 | 12/2011 | Cales et al. | |

(Continued)

FOREIGN PATENT DOCUMENTS

| | | |
|---|---|---|
| CN | 102302358 A | 1/2012 |
| CN | 102334122 A | 1/2012 |

(Continued)

OTHER PUBLICATIONS

Written Opinion issued on Mar. 28, 2019 in corresponding International application No. PCT/CN2019/072227; 7 pages.

(Continued)

*Primary Examiner* — Kaitlyn E Sebastian
(74) *Attorney, Agent, or Firm* — Maier & Maier, PLLC

(57) ABSTRACT

A method and device for detecting tissue fibrosis. The method includes: determining whether there is a possibility for tissue inflammation; and when there is a possibility for tissue inflammation, monitoring tissue stiffness or a parameter reflecting tissue stiffness during a treatment of the tissue inflammation to determine whether the tissue inflammation has been eliminated; when the tissue inflammation has been eliminated or there is no possibility for tissue inflammation, obtaining a degree of tissue fibrosis or information related to the degree of tissue fibrosis according to tissue stiffness or a parameter reflecting tissue stiffness. The embodiments enable the tracking of the tissue stiffness during the treatment of tissue inflammation to determine whether tissue inflammation has been eliminated or not, and since tissue stiffness can be detected by a non-invasive quantitative (Continued)

detection technique of tissue elastic modulus, avoiding defects caused by tissue biopsy.

6 Claims, 5 Drawing Sheets

(56) References Cited

U.S. PATENT DOCUMENTS

| | | | | |
|---|---|---|---|---|
| 2013/0202619 | A1* | 8/2013 | Charlton | C12N 5/067 435/6.13 |
| 2014/0094702 | A1* | 4/2014 | Kim | A61B 8/4281 600/438 |
| 2015/0148658 | A1* | 5/2015 | Smith | G06T 7/0012 600/443 |
| 2015/0148671 | A1 | 5/2015 | Chen et al. | |
| 2015/0369820 | A1* | 12/2015 | Møller | H01J 49/0027 435/5 |
| 2018/0098728 | A1* | 4/2018 | Cales | A61B 5/7264 |
| 2018/0296546 | A1* | 10/2018 | Guo | A61K 31/4439 |
| 2019/0076128 | A1* | 3/2019 | Hah | A61B 8/085 |
| 2019/0265241 | A1* | 8/2019 | Poynard | G16H 50/30 |

FOREIGN PATENT DOCUMENTS

| | | |
|---|---|---|
| CN | 108095767 A | 6/2018 |
| CN | 108309348 A | 7/2018 |
| CN | 108378870 A | 8/2018 |
| WO | 2010058295 A2 | 5/2010 |

OTHER PUBLICATIONS

Chinese Office Action issued on Dec. 25, 2019 in corresponding Chinese application No. 201810055510.7: 15 pages.
Tang Yanfang et al., "The value of FibroTouch and FIB-4 in the diagnosis of chronic hepatitis B fibrosis", Department of Liver Diseases, Ruikang Hospital, Guangxi University of Traditional Chinese Medicine, Sep. 2017, 1 pg.
Examination Report issued on Apr. 11, 2019 of corresponding Chinese application No. 201810055510.7; 5 pages.
International Search Report issued on Mar. 28, 2019 in corresponding International application No. PCT/CN2019/072227; 10 pages.

* cited by examiner

METHOD AND DEVICE FOR DETECTING TISSUE FIBROSIS

CROSS-REFERENCE TO RELATED APPLICATIONS

This application is a continuation of International Application No. PCT/CN2019/072227, filed on Jan. 17, 2019, which claims priority to Chinese Patent Application No. 201810055510.7, filed on Jan. 19, 2018, both of which are hereby incorporated by reference in their entireties.

FIELD

The disclosure relates to the field of measurement, and in particular, to a method and device for detecting tissue fibrosis.

BACKGROUND

The development of various chronic liver diseases such as viral hepatitis (hepatitis A, hepatitis B, hepatitis C, etc.) is accompanied by fibrosis of the liver, the liver fibrosis process is accompanied by changes of liver elasticity. Therefore, liver elasticity information is a parameter that can be used to diagnose the degree of liver fibrosis.

Transient Elastography (TE) technique is a technique to quantitatively measure the elastic modulus of a tissue and provides a more complete picture of the degree of liver fibrosis by measuring Liver Stiffness measurement (LSM).

Diagnosis of liver fibrosis by LSM is susceptible to liver inflammation. Currently, clinical pathological examination, i.e. liver biopsy, is a commonly used way to evaluate liver inflammation. However, liver biopsy has many limiting factors, its invasive drawbacks, risk of complications make it impossible to perform continuous liver biopsy to evaluate the liver inflammation in routine clinical practice, and liver biopsy is also affected by sampling errors. Therefore, it is imperative to find a new and non-invasive evaluation way for tissue inflammation.

SUMMARY

Embodiments of the disclosure provide a method and device for detecting tissue fibrosis. In order to provide a basic understanding of some aspects of the disclosed embodiments, a brief summary is given below. This summary section is not intended to be a general commentary, nor is it to identify key/important elements or to depict the protection scope of these embodiments. Its sole purpose is to present some concepts in a simple form as a preface to the following detailed description.

In a first aspect, an embodiment of the present disclosure provides a method for detecting tissue fibrosis, the method including:

determining whether there is a possibility for tissue inflammation;

monitoring tissue stiffness or a parameter reflecting tissue stiffness during a treatment of the tissue inflammation to determine whether the inflammation has been eliminated, when there is a possibility for tissue inflammation;

obtaining a degree of tissue fibrosis or information related to the degree of tissue fibrosis according to tissue stiffness or a parameter reflecting tissue stiffness, when the tissue inflammation has been eliminated or there is no possibility for inflammation.

Based on the method, as an optional first embodiment, the method further including:

considering the inflammation has been eliminated if the tissue stiffness or the parameter reflecting tissue stiffness continues to decline and reaches a platform value during the treatment of tissue inflammation.

Based on the method, as an optional second embodiment, the method further including:

obtaining inflammation activity of a tissue or inflammation activity related information of a tissue according to the tissue stiffness or the parameter reflecting tissue stiffness that detected, when there is a possibility for tissue inflammation.

Based on the second embodiment, as an optional third embodiment, the obtaining inflammation activity of a tissue or inflammation activity related information of a tissue according to the tissue stiffness or the parameter reflecting tissue stiffness that detected including:

obtaining the inflammation activity of a tissue or inflammation activity related information of a tissue according to a preset corresponding relationship between the tissue stiffness or the parameter reflecting tissue stiffness and the inflammation activity of a tissue or inflammation activity related information of a tissue.

Based on the third embodiment, as an optional fourth embodiment, the corresponding relationship includes:

a liver stiffness value LSM of 6.1-8.7 Kpa corresponds to mild tissue inflammatory necrosis;

an LSM of 8.7-13.2 Kpa corresponds to moderate tissue inflammatory necrosis;

an LSM of 13.2 Kpa or more corresponds to severe tissue inflammatory necrosis.

Based on the third embodiment, as an optional fifth embodiment, the corresponding relationship includes: the tissue stiffness or the parameter reflecting tissue stiffness and inflammation activity of a tissue or inflammation activity related information of a tissue corresponding to a different etiology.

Based on the third embodiment, as an optional sixth embodiment, a method of setting up the corresponding relationship, including:

using a data of a subject to establish a Receiver Operating Characteristic curve;

using the inflammation activity of a tissue based on a pathological examination and the Receiver Operating Characteristic curve to obtain a sensitivity, a specificity, a positive predictive value and a negative predictive value of the tissue stiffness or the parameter reflecting tissue stiffness for inflammation activity of each tissue;

using the sensitivity and specificity to determine the Youden index for the inflammation activity of each tissue;

using the Youden index to determine a corresponding dividing value for the tissue stiffness or the parameter reflecting tissue stiffness.

Based on the method, as an optional seventh embodiment, the determining whether there is a possibility for tissue inflammation, including:

determining whether there is clinical confirmation of abnormal tissue status;

determining whether inflammation related parameters are indicative of the presence of inflammation, when there is clinical confirmation of abnormal tissue status;

determining there is a possibility for tissue inflammation, when the inflammation related parameters indicate the presence of inflammation.

Based on the method, as an optional eighth embodiment, the determining whether there is a possibility for tissue inflammation, including:

determining whether there is clinical confirmation of abnormal tissue status;

determining whether inflammation related parameters are indicative of the presence of inflammation, when there is clinical confirmation of abnormal tissue status;

monitoring whether there is an abnormal and sustained increase in the tissue stiffness within a first set period of time, when the inflammation related parameter indicates that inflammation is absent;

determining there is a possibility for tissue inflammation, when the abnormal and sustained increase in the tissue stiffness within the first set period of time is monitored.

Based on the method, as an optional ninth embodiment, the determining whether there is a possibility for tissue inflammation, including:

confirming whether a clinical antiviral tissue inflammation treatment has been administered;

determining there is a possibility for tissue inflammation in a process of clinical antiviral tissue inflammation treatment or within a preset time after the clinical antiviral tissue inflammation treatment.

In a second aspect, an embodiment of the present disclosure provides a device for detecting tissue fibrosis, the device including:

a memory, configured to store operation instructions;

a processor, configured to execute the operation instructions in the memory to accomplish the following operations:

determining whether there is a possibility for tissue inflammation;

monitoring tissue stiffness or a parameter reflecting tissue stiffness during a treatment of the tissue inflammation to determine whether the inflammation has been eliminated, when there is a possibility for tissue inflammation;

obtaining a degree of tissue fibrosis or information related to the degree of tissue fibrosis according to tissue stiffness or a parameter reflecting tissue stiffness, when the tissue inflammation has been eliminated or there is no possibility for inflammation.

In a third aspect, an embodiment of the present disclosure provides a device for detecting tissue fibrosis, the device including:

a receiver, configured to receive the tissue stiffness detected from a detection probe;

a processor, configured to determine whether there is a possibility for tissue inflammation; monitor tissue stiffness during a treatment of the tissue inflammation, when there is a possibility for tissue inflammation; if the monitored tissue stiffness is normal and reaches a platform value, determine the degree of tissue fibrosis based on the platform value; when the tissue inflammation is absent, determine the degree of tissue fibrosis based on the detected tissue stiffness.

The method and device for detecting tissue fibrosis in the embodiments of the present disclosure, enables the tracking and monitoring the tissue stiffness or the parameter reflecting tissue stiffness during the treatment of tissue inflammation to determine whether tissue inflammation has been eliminated, and since the tissue stiffness or the parameter reflecting tissue stiffness can be detected by means of a non-invasive quantitative detection technique of tissue elastic modulus, avoiding defects caused by tissue biopsy, and can evaluate the tissue inflammation non-invasively, continuously and accurately.

It should be understood that the above general description and the following detailed description are only exemplary and explanatory, and do not limit the present disclosure.

BRIEF DESCRIPTION OF THE DRAWINGS

The drawings here are incorporated into and constitute a part of this specification, showing embodiments that are consistent with the present disclosure, and are used together with the specification to explain the principles of the present disclosure.

DETAILED DESCRIPTION OF THE EMBODIMENTS

Figure 1:
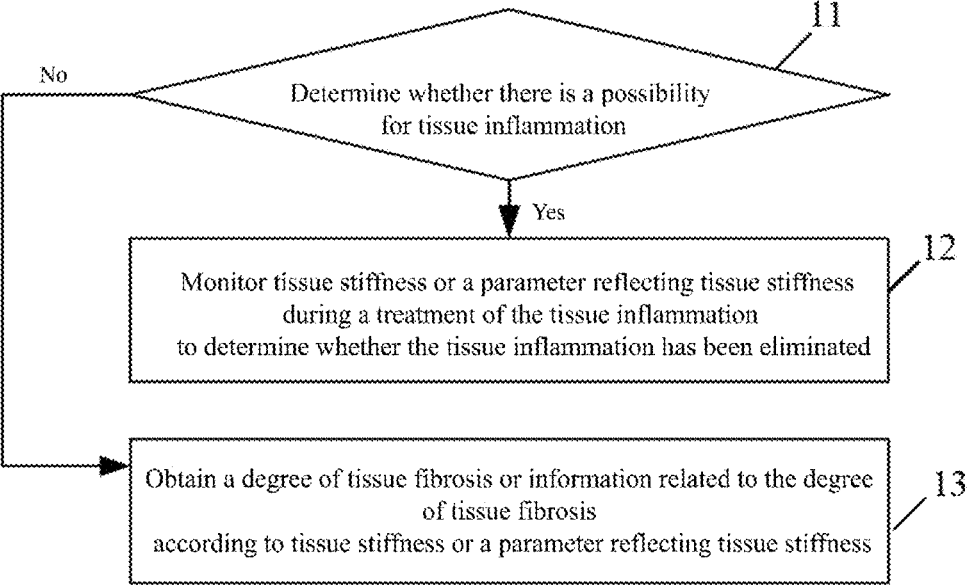
FIG. 1 is a flow chart of a method for detecting tissue fibrosis in an exemplary embodiment.

The following description and the drawings sufficiently illustrate specific embodiments of the present disclosure to enable those skilled in the art to practice them. The embodiments represent only possible changes. Unless specifically required, individual components and functions are optional, and the order of operations may vary. Parts and features of some embodiments may be included in or substituted for parts and features of other embodiments. The scope of the embodiments of the present disclosure includes the entire scope of the claims, and all available equivalents of the claims. In this text, various embodiments may be expressed individually or collectively in term of "disclosure", which is for convenience only, and if more than one disclosure is actually disclosed, it is not intended to automatically limit the scope of the application to any single disclosure or inventive concept. In this text, relational terms such as first and second are used only to distinguish one entity or operation from another entity or operation, and do not require or imply any actual relationship between these entities or operations or order. Moreover, the terms "comprise", "include" or any other variant thereof are intended to cover non-exclusive inclusion, so that a process, method, or device that includes a set of elements includes not only those elements, but also other elements not explicitly listed. The embodiments in this text are described in a progressive manner, each embodiment focuses on the differences from other embodiments, and the same and similar parts between the embodiments can be referred to each other. For the structures and products disclosed in the embodiments, since they correspond to the parts disclosed in the embodiments, the description is relatively simple, and the relevant part can be referred to the description in the method part.

The applicant has broken away from the inherent thinking in the field by years of in-depth research on a large number of clinical data, and has achieved the quantitative evaluation of tissue inflammation and provided a new perspective for quantitative evaluation of tissue inflammation by applying the tissue stiffness parameters that used to evaluate tissue fibrosis to the evaluation of tissue inflammation. At the same time, combined with non-invasive tissue stiffness detection based on tissue elastography technology, instead of liver puncture tissue stiffness detection, a scheme of grading evaluation of tissue inflammation in a non-invasive manner thus can be realized. The technical scheme is reasonable and efficient, and has extremely important medical value.

The present disclosure is not used to directly diagnose or treat diseases, but focus on the physical parameters of inflammation, and provides a new perspective of quantitative evaluation scheme of tissue inflammation, which breaks the inherent thinking; at the same time, implementing non-invasive tissue stiffness detection based on tissue elastography technology, instead of liver puncture tissue stiffness detection, the purpose of grading evaluation of tissue inflammation parameters in a non-invasive manner thus can be realized.

In an exemplary embodiment, as shown in FIG. 1, the method for detecting tissue fibrosis includes the following steps.

In step 11, determining whether there is a possibility for tissue inflammation; when there is a possibility for tissue inflammation, perform step 12; when the tissue inflammation has been eliminated or there is no possibility for inflammation, perform step 13.

In step 12, monitoring tissue stiffness or a parameter reflecting tissue stiffness during a treatment of the tissue inflammation to determine whether the tissue inflammation has been eliminated.

In step 13, obtaining a degree of tissue fibrosis or information related to the degree of tissue fibrosis according to tissue stiffness or a parameter reflecting tissue stiffness.

Obtaining the degree of tissue fibrosis or information related to the degree of tissue fibrosis according to the tissue stiffness or the parameter reflecting the tissue stiffness can be achieved in the usual ways.

In the present exemplary embodiment, the tissue includes tissues and organs such as liver, lung and the like. Tissue stiffness or a parameter reflecting tissue stiffness can be detected by means of a quantitative detection technique of tissue elastic modulus. Specifically, non-invasive tissue stiffness detection can be achieved through applicant's self-developed non-invasive liver function detector, FibroTouch.

In this exemplary embodiment, tissue stiffness or a parameter reflecting tissue stiffness can be tracked and monitored during the treatment of tissue inflammation to determine whether the tissue inflammation has been eliminated, and since the tissue stiffness or the parameter reflecting tissue stiffness can be detected by means of a non-invasive quantitative detection technique of tissue elastic modulus, avoiding defects caused by tissue biopsy, and can evaluate the tissue inflammation non-invasively, continuously and accurately.

The inflammation activity of a tissue is an important parameter for evaluating tissue inflammation. The tissue stiffness or the parameter reflecting tissue stiffness can be further utilized to determine the inflammation activity of a tissue or the inflammation activity related information of a tissue, when there is a possibility for tissue inflammation. The following are some examples of using the tissue stiffness to determine the inflammation activity of a tissue.

In an exemplary embodiment, the tissue is a liver, and inspectors can obtain the LSM of the liver by an instantaneous elastic detection equipment. The above-mentioned instantaneous elastic detection equipment may include a probe and a host, inspectors may hold the probe in contact with an area of human skin where the liver is located, ultrasound and shear waves are emitted to the liver by the probe, and the echo signal of the received ultrasound is sent to the host. By analyzing the above echo signals, the host obtains the LSM of the liver, which can be acquired at any time and continuously using instantaneous elastic detection equipment.

In this exemplary embodiment, the inflammation activity of a tissue may include: mild tissue inflammatory necrosis (G≥1), moderate tissue inflammatory necrosis (G≥2), and severe tissue inflammatory necrosis (G≥3).

Figure 2:
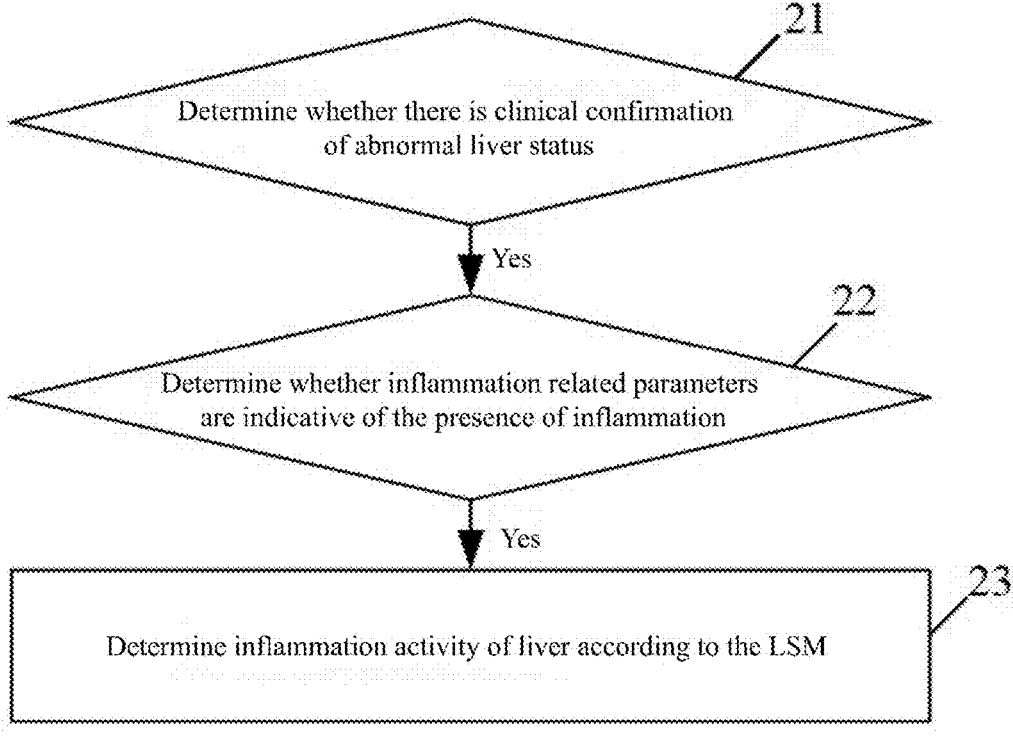
FIG. 2 is a flow chart of a method for detecting inflammation activity of a tissue in an exemplary embodiment.

FIG. 2 is a flow chart of a method for detecting inflammation activity of a tissue in an exemplary embodiment, the method includes the following steps.

In step 21, determining whether there is clinical confirmation of abnormal liver status, and if there is clinical confirmation of abnormal liver status, perform step 22.

In this step, whether the liver status is abnormal may be confirmed clinically by a number of ways, such as serum analysis or clinical symptoms, and etc.

In step 22, determining whether inflammation related parameters are indicative of the presence of inflammation, and if the inflammation related parameters indicate the presence of inflammation, perform step 23.

In this step, the inflammation related parameters include: alanine aminotransferase (ALT) and aspartate aminotransferase (AST). ALT and AST are mainly distributed in hepatocytes, and elevated ALT and AST indicate hepatocyte damage. ALT is the most sensitive. A doubling of ALT in serum indicates hepatocellular necrosis in 1%. ALT and AST are usually elevated to a degree consistent with hepatocyte damage. ALT is mainly distributed in hepatocyte plasma. Elevated ALT reflects damage to hepatocyte membranes, and AST is predominantly found in hepatocyte plasma and hepatocyte mitochondria. Therefore, the elevated ALT and AST are different in different inflammatory conditions of the liver, and the ratio of ALT to AST is also different. The presence of liver inflammation can be determined using different inflammation related parameters.

ALT is used to determine the presence of liver inflammation as an example. The normal value of ALT is influenced by various factors such as age, gender and the like, at the same time, and the baseline level of ALT varies greatly among different individuals. In practical applications, ALT is not a completely accurate reflection of the "infiltration of inflammatory cells" of liver, and a significant proportion of patients have a liver biopsy revealed moderate to severe "infiltration of inflammatory cells" of liver, but their ALT is still at normal level, i.e. less than or equal to 40 U/L. Therefore, when ALT is abnormal, it can be determined that the liver inflammation is presence, but when the ALT is normal, it is needed to further determine whether the liver inflammation is presence, for normal ALT, it will be described in other exemplary embodiments below.

In step 23, determining inflammation activity of liver according to the LSM.

In this step, the inflammation activity of liver is determined based on the preset corresponding relationship between the LSM and the inflammation activity of liver.

As an optional embodiment, when the LSM is 6.1-8.7 Kpa, the corresponding inflammation activity of tissue is mild tissue inflammatory necrosis, when the LSM is 8.7-13.2 Kpa, the corresponding inflammation activity of tissue is moderate tissue inflammatory necrosis, when the LSM is 13.2 Kpa or more, the corresponding inflammation activity of tissue is severe tissue inflammatory necrosis.

Furthermore, the corresponding relationship between the LSM and the inflammation activity of liver can be preset for different etiologies, respectively.

As shown in Table 1 below, an example of the above corresponding relationship is given, where the dividing value refers to the critical value of LSM, the sensitivity refers to the actual percentage of people who are sick and judged to be sick by experimental standard, and the specificity refers to the actual percentage of people who are free of disease and correctly judged to be free of disease by experimental standards. Positive predictive value (PPV) and negative predictive value (NPV) reflect the diagnostic value of indicators in the real world, with higher the value representing the higher the diagnostic value. Sensitivity, specificity, PPV and NPV can use liver biopsy results as the gold standard and be calculated by using ROC curve, which represents the sensitivity, specificity, PPV and NPV of LSM to G2 and G3. It can be seen that Table 1 gives the corresponding relationship between LSM and activities of liver inflammatory for different etiologies, the dividing value corresponding to each level of inflammation activity of liver represents the minimum LSM that required for that level. For example, for a patient with viral hepatitis, after performing step 21 and step 22, if the LSM detected is 10, the level of inflammation activity of liver for this patient will be determined as G2.

TABLE 1

| Etiology | Level of inflammation activity of liver | Area under the curve | Dividing value | Sensitivity (%) | Specificity (%) | PPV | NPV |
|---|---|---|---|---|---|---|---|
| total | G ≥ 2 | 0.797 (0.763-0.828) | 8.7 | 66.67 | 82.33 | 83.2 | 65.4 |
|  | G ≥ 3 | 0.791 (0.757-0.823) | 13.2 | 61.07 | 83.02 | 49.4 | 88.7 |
| ALT ≤ 40 U/L | G ≥ 2 | 0.726 (0.666-0.781) | 9.3 | 54.95 | 84.85 | 75.3 | 69.1 |
|  | G ≥ 3 | 0.802 (0.747-0.851) | 10.7 | 70.97 | 79.72 | 33.9 | 94.9 |
| viral hepatitis | G ≥ 2 | 0.832 (0.784-0.873) | 8.7 | 72.15 | 84.06 | 83.8 | 72.5 |
|  | G ≥ 3 | 0.851 (0.805-0.890) | 13.2 | 78.38 | 80.69 | 36.7 | 96.3 |
| non-alcohol fatty liver disease | G ≥ 2 | 0.814 (0.728-0.883) | 8.7 | 61.11 | 85.92 | 68.7 | 81.3 |
|  | G ≥ 3 | 0.862 (0.782-0.921) | 9.7 | 83.33 | 80.20 | 20.0 | 98.8 |
| autoimmune hepatitis | G ≥ 2 | 0.880 (0.777-0.947) | 6.1 | 80.00 | 90.91 | 97.8 | 47.6 |
|  | G ≥ 3 | 0.907 (0.810-0.965) | 10.1 | 81.82 | 90.91 | 90.0 | 83.3 |
| primary biliary cholangitis | G ≥ 2 | 0.815 (0.710-0.894) | 6.8 | 71.43 | 85.71 | 95.7 | 40.0 |
|  | G ≥ 3 | 0.732 (0.619-0.827) | 9.2 | 54.05 | 77.50 | 69.0 | 64.6 |
| others | G ≥ 2 | 0.783 (0.666-0.874) | 10.6 | 77.78 | 75.00 | 77.8 | 75.0 |
|  | G ≥ 3 | 0.812 (0.699-0.896) | 14.3 | 83.33 | 78.00 | 57.7 | 92.9 |

The above Table 1 needs to be pre-set prior to implementing the method of this exemplary embodiment, and the data on which the setting is based is obtained through experiments.

The subjects of the experiment were 614 patients who had liver biopsies, including 296 cases of viral hepatitis, 66 cases of autoimmune hepatitis, 77 cases of primary biliary cholangitis, 107 cases of non-alcoholic fatty liver disease, and 68 cases of chronic liver disease from other causes (drug-induced liver disease and liver disease of unknown etiology). The basic profile of these subjects is given in Table 2 below, where the inflammation activity of liver was obtained by liver biopsy of the patients.

TABLE 2

|  | total (n = 614) | viral hepatitis (n = 296) | autoimmune hepatitis (n = 66) | primary biliary cholangitis (n = 77) | non-alcohol fatty liver disease (n = 107) | others (n = 68) | p-value |
|---|---|---|---|---|---|---|---|
| Gender (male/female) | 300/314 | 190/106 | 12/54 | 12/65 | 59/48 | 27/41 | 0.000 |
| age | 42 (30, 51) | 37 (27, 46) | 49 (39, 56) | 50 (42, 55) | 40 (26, 51) | 48 (39, 52) | 0.000 |
| LSM (Kpa) | 8.1 (5.8, 14.1) | 8.2 (5.9, 14.1) | 8.5 (5.6, 15.6) | 7.6 (5.7, 11.8) | 6.9 (5.4, 9.5) | 12.2 (6.4, 17.9) | 0.993 |
| ALT (U/L) | 53 (28, 119) | 41 (25, 84) | 103 (41, 194) | 58 (25, 112) | 76 (40, 118) | 58 (35, 176) | 0.112 |
| AST (U/L) | 40 (27, 78) | 34 (24, 63) | 74 (33, 154) | 55 (35, 103) | 44 (30, 65) | 54 (32, 120) | 0.003 |
| Level of inflammation activity of liver (G0-1/G2/G3-4) | 266/217/131 | 138/121/37 | 11/22/33 | 14/26/37 | 71/30/6 | 32/18/18 | 0.000 |

9

Figure 3:
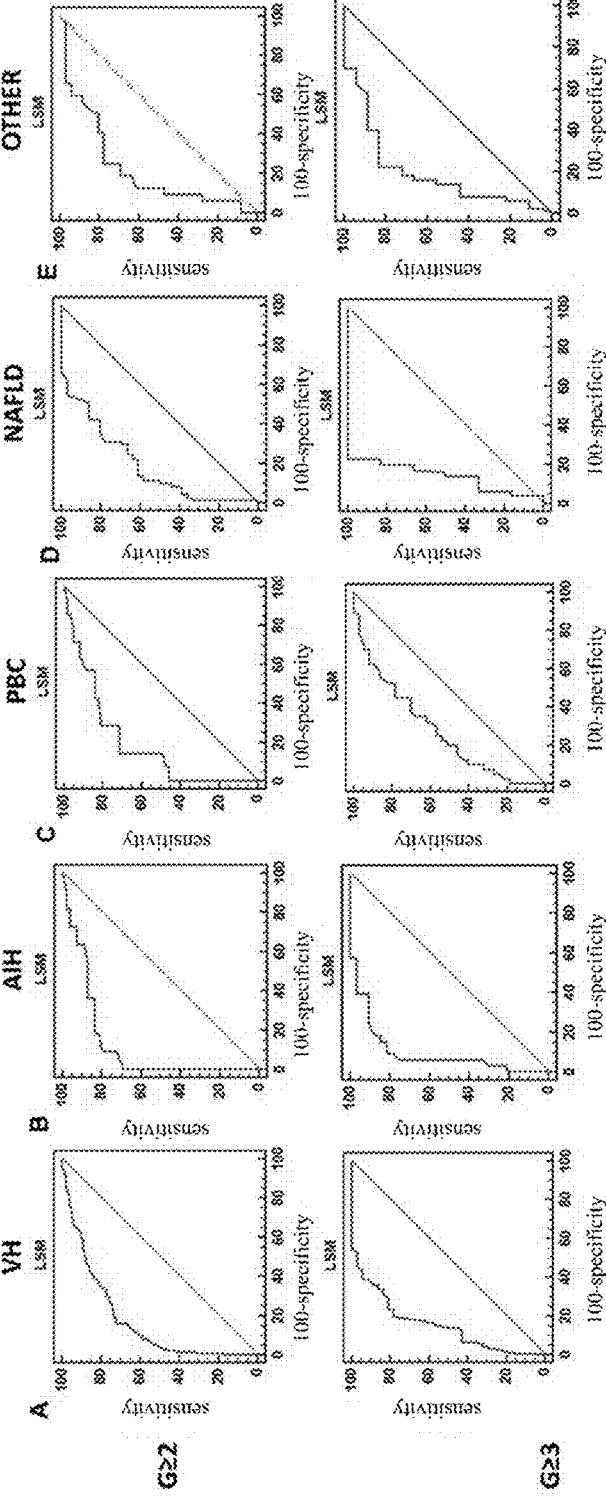
FIG. 3 is a schematic diagram of the ROC (Receiver Operating Characteristic) curve in an exemplary embodiment.

Based on the experimental data of the research subject, for each etiology, corresponding relationship in the previous text can be set as the following the steps 1)-3):

1) Using the data of a subject to establish the Receiver Operating Characteristic (ROC) curve; FIG. 3 shows an example of the ROC curve, wherein, the horizontal coordinates of the curve are 100-specificity and the vertical coordinates are sensitivity, VH represents patients with viral hepatitis, AIH represents patients with autoimmune hepatitis, PBC represents patients with primary biliary cholangitis, NAFLD represents patients with non-alcoholic fatty liver disease, and OTHER represents patients with liver disease of other etiologies (non-alcoholic fatty liver, drug-induced liver disease and liver disease of unknown etiology);

2) Using the ROC curve to determine the Youden index; the Youden index refers to the sum of sensitivity and specificity minus 1;

3) Determining the LSM corresponding to the Yoden Index as the dividing value.

In the above step 1), SPSS21.0 (SPSS, Chicago, Illinois, USA) statistical software can be used for statistical analysis, continuous variables choose the description method according to their distribution characteristics, the quantitative data that approximately follow the normal distribution are represented as x̄±S, the distribution characteristics of the quantitative data that follow the skewed distribution is described by using the median (M) and interquartile range, $\chi^2$ test is used to compare the qualitative data between groups, and the Mann-Whitny U test is used to compare two independent samples, the Kruskal Wallis test is used to compare multiple samples. ROC curves were established to compare the assessed value of different indicators of the inflammation activity of liver based on the area under the ROC curve, with $\alpha=0.05$ test level.

The experiment shows that among the 614 patients with chronic liver disease, 348 (56.7%) patients have moderate and above inflammatory necrosis (G≥2). 305 of 348 (87.6%) patients with moderate and above inflammatory necrosis have an elevated LSM (LSM>6.1 Kpa), and 242 (69.5%) patients have an elevated ALT (ALT>40 U/L), 91 of 111 patients (82.0%) with moderate and above inflammatory necrosis and normal ALT have an elevated LSM. This data shows that LSM is more sensitive than serum ALT for detecting moderate inflammatory necrosis.

In an exemplary embodiment, the tissue is a liver, and inspectors can obtain the LSM of the liver by the instantaneous elastic detection equipment. The above-mentioned instantaneous elastic detection equipment may include a probe and a host, inspectors may hold the probe in contact with the area of human skin where the liver is located, ultrasound and shear waves are emitted to the liver by the probe, and the echo signal of the received ultrasound is sent to the host. By analyzing the above echo signals, the host obtains the LSM of the liver, which can be acquired at any time and continuously using instantaneous elastic detection equipment.

In this exemplary embodiment, the inflammation activity of a tissue may include: mild tissue inflammatory necrosis (G≥1), moderate tissue inflammatory necrosis (G≥2), and severe tissue inflammatory necrosis (G≥3).

In this exemplary embodiment, a sensitive and efficient diagnosis of chronic hepatitis patients with normal inflammation related parameters who are unable to determine inflammation activity of liver can be achieved by detecting the quantifiable indicators of inflammation activity of liver.

10

Figure 4:
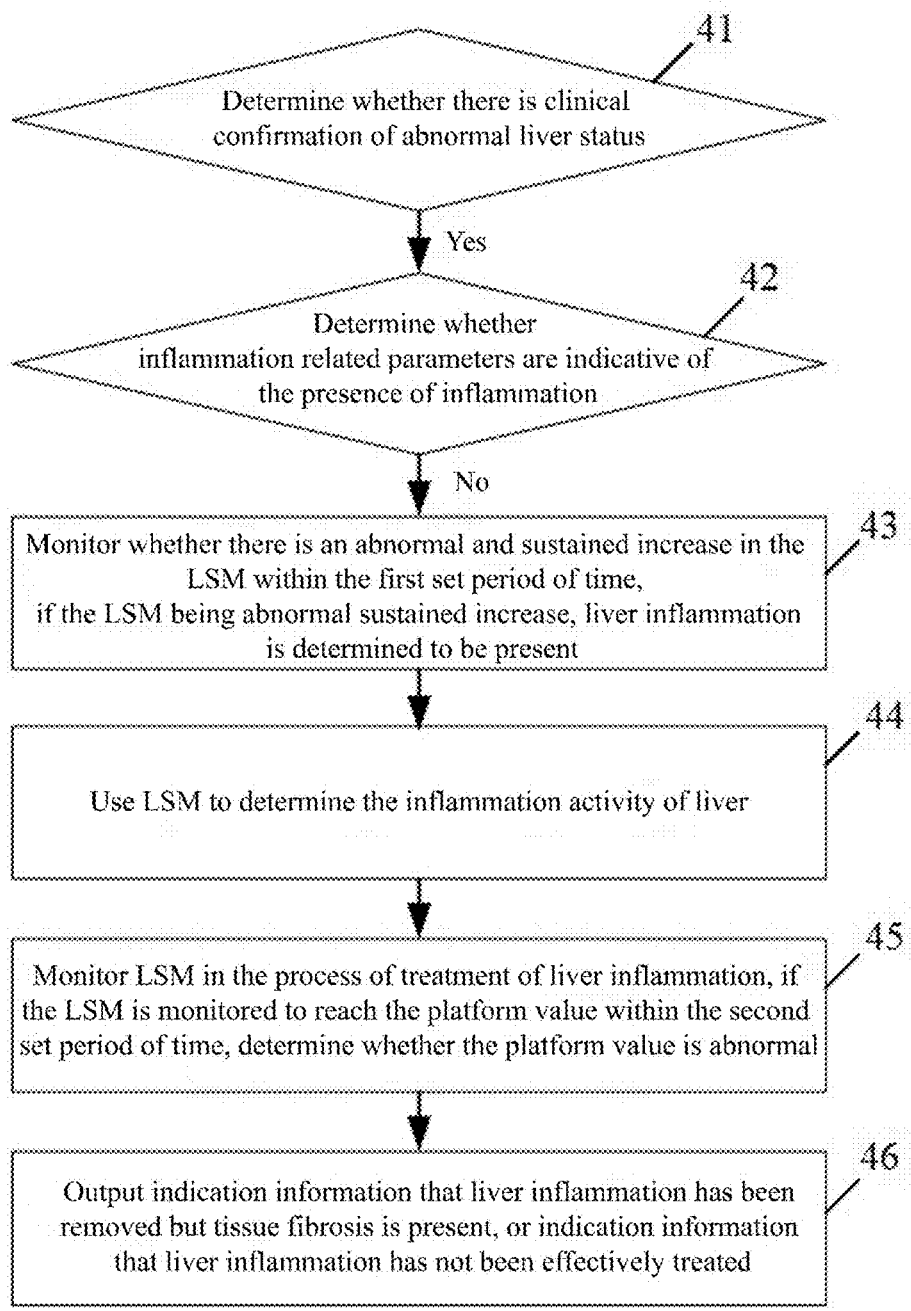
FIG. 4 is a flow chart of a method for detecting inflammation activity of a tissue in an exemplary embodiment.

FIG. 4 is a flow chart of a method for detecting inflammation activity of a tissue in an exemplary embodiment, the method includes the following steps.

In step 41, determining whether there is clinical confirmation of abnormal liver status, and if there is clinical confirmation of abnormal liver status, perform step 42.

In this step, whether the liver status is abnormal may be confirmed clinically by a number of ways, such as serum analysis or clinical symptoms, and etc.

In step 42, determining whether inflammation related parameters are indicative of the presence of inflammation, and if the inflammation related parameters indicate the absence of inflammation, perform step 43.

In this step, ALT is also used to determine the presence of liver inflammation as an example. The normal value of ALT is influenced by various factors such as age, gender and the like, at the same time, and the baseline level of ALT varies greatly among different individuals. In practical applications, ALT is not a completely accurate reflection of the "infiltration of inflammatory cells" of liver, and a significant proportion of patients have a liver biopsy revealed moderate to severe "infiltration of inflammatory cells" of liver, but their ALT is still at normal level, i.e. less than or equal to 40 U/L. Therefore, when ALT is abnormal, it can be determined that the liver inflammation is presence, but when the ALT is normal, it is needed to further determine whether liver inflammation is presence.

In step 43, monitoring whether there is an abnormal and sustained increase in the LSM within the first set period of time, if the LSM being abnormal and sustained increase, liver inflammation is determined to be present.

In this step, abnormal means higher than normal value.

In this step, the first set period of time is a custom setting value, for example, 3 months, and LSM needs to be continuously monitored during the first set period of time. Through experiments, it is known that LSM is abnormal and elevated with the increase of inflammation activity of liver, and is significantly positively correlated with the inflammation activity of liver, therefore, if the LSM being abnormal and persistently elevated, liver inflammation can be determined to be present.

In step 44, using LSM to determine the inflammation activity of liver.

In this step, the inflammation activity of liver is determined according to the preset corresponding relationship between the LSM and the inflammation activity of liver.

As an optional embodiment, when the LSM is 6.1-8.7 Kpa, the corresponding inflammation activity of tissue is mild tissue inflammatory necrosis, when the LSM is 8.7-13.2 Kpa, the corresponding inflammation activity of tissue is moderate tissue inflammatory necrosis, when the LSM is 13.2 Kpa or more, the corresponding inflammation activity of tissue is severe tissue inflammatory necrosis Furthermore, the corresponding relationship between LSM and inflammation activity of liver can be preset for different etiologies, respectively.

The method of setting up the above corresponding relationship is the same as that described above, and will not be repeated here.

In step 45, monitoring LSM in the process of treatment of liver inflammation, if the LSM is monitored to reach the platform value within the second set period of time, determine whether the platform value is abnormal, and if the platform value is abnormal, perform step 46.

In this step, abnormal means higher than normal value.

In this step, the second set period of time is a custom setting value, for example, half a year, if the LSM is monitored to reach a platform value and abnormal during the second set period of time, this indicates that liver inflammation has not been effectively treated or live fibrosis is present.

In step 46, determining live fibrosis is present or liver inflammation has not been effectively treated.

In an exemplary embodiment, the tissue is a liver, and inspectors can obtain the LSM of the liver by the instantaneous elastic detection equipment. The above-mentioned instantaneous elastic detection equipment may include a probe and a host, inspectors may hold the probe in contact with the area of human skin where the liver is located, ultrasound and shear waves are emitted to the liver by the probe, and the echo signal of the received ultrasound is sent to the host. By analyzing the above echo signals, the host obtains the LSM of the liver, which can be acquired at any time and continuously using instantaneous elastic detection equipment.

In this exemplary embodiment, the activities tissue inflammation may include: mild tissue inflammatory necrosis (G≥1), moderate tissue inflammatory necrosis (G≥2), and severe tissue inflammatory necrosis (G≥3).

In the present exemplary embodiment, for viral hepatitis, and after taking antiviral treatment, the therapeutic effect can be sensitively and efficiently judged by detecting the quantifiable indicators of inflammation activity of liver.

Figure 5:
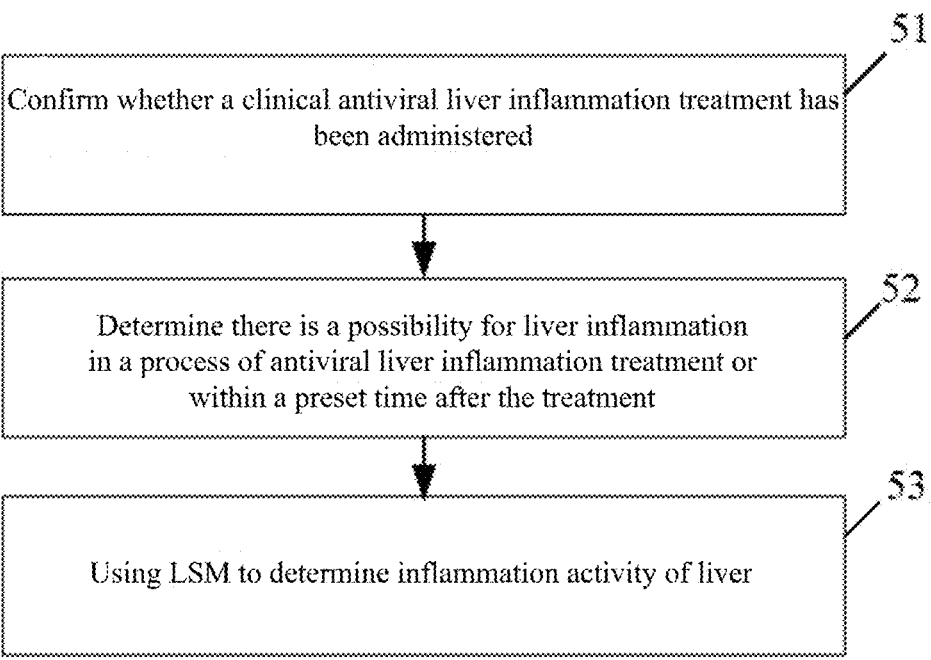
FIG. 5 is a flow chart of a method for detecting inflammation activity of a tissue in an exemplary embodiment.

FIG. 5 is a flow chart of a method for detecting inflammation activity of a tissue in an exemplary embodiment, the method includes the following steps.

In step 51, confirming whether a clinical antiviral liver inflammation treatment has been administered, in a process of antiviral liver inflammation treatment or within a preset time after the treatment, perform step 52.

In this step, when the virus is eliminated after treatment, the inflammation cannot be eliminated quickly, therefore, it is possible to confirm that there is a possibility for liver inflammation, when the antiviral liver inflammation treatment has been administered.

In step 52, determining there is a possibility for liver inflammation.

In step 53, using LSM to determine inflammation activity of liver.

In this step, the inflammation activity of liver is determined according to the preset corresponding relationship between the LSM and the inflammation activity of liver.

As an optional embodiment, when the LSM is 6.1-8.7 Kpa, the corresponding inflammation activity of tissue is mild tissue inflammatory necrosis, when the LSM is 8.7-13.2 Kpa, the corresponding inflammation activity of tissue is moderate tissue inflammatory necrosis, when the LSM is 13.2 Kpa or more, the corresponding inflammation activity of tissue is severe tissue inflammatory necrosis.

Furthermore, the corresponding relationship between LSM and inflammation activity of liver can be preset for different etiologies, respectively.

The method of setting the above corresponding relationship is the same as that described above, and will not be repeated here.

The exemplary embodiments of the method described above may be implemented by software algorithms, and the device for detecting tissue fibrosis may include: a memory and a processor.

the memory, configured to store operation instructions.

the processor, configured to execute the operation instructions in the memory to accomplish the content described in the method steps in the foregoing exemplary embodiments.

The exemplary embodiments of the method described above may be implemented by a device for detecting tissue fibrosis, and the device for detecting tissue fibrosis includes: a receiver and a processor. The device for detecting tissue fibrosis may be located on one side of the host.

The receiver, configured to receive tissue stiffness detected from a detection probe.

The processor, configured to complete the content described in the method steps in the foregoing exemplary embodiments.

It should be understood that the present disclosure is not limited to the processes and structures already described above and shown in the drawings, and various modifications and changes can be made without departing from the scope thereof. The scope of the disclosure is only limited by the appended claims.

What is claimed is:

1. A method for detecting tissue fibrosis, wherein the method is performed through a device for detecting tissue fibrosis, the device comprises a processor, the processor is configured to execute the following operations: determining whether there is a tissue inflammation; monitoring tissue stiffness or a parameter reflecting tissue stiffness during a treatment of the tissue inflammation to determine whether the tissue inflammation has been eliminated when there is a tissue inflammation; and obtaining a degree of tissue fibrosis or information related to the degree of tissue fibrosis according to tissue stiffness or a parameter reflecting tissue stiffness when the tissue inflammation has been eliminated or there is no tissue inflammation; obtaining of inflammation activity of a tissue or inflammation activity related information of a tissue according to the detected tissue stiffness or the detected parameter reflecting tissue stiffness when there is a tissue inflammation; wherein the obtaining of inflammation activity of a tissue or inflammation activity related information of a tissue according to the detected tissue stiffness or the detected parameter reflecting tissue stiffness comprises: obtaining the inflammation activity of a tissue or inflammation activity related information of a tissue according to a preset corresponding relationship between the tissue stiffness or the parameter reflecting tissue stiffness and the inflammation activity of a tissue or inflammation activity related information of a tissue; determining the presence of liver inflammation through alanine aminotransferase (ALT), determining the ALT is abnormal and liver inflammation is present when the ALT is greater than 40 U/L; determining the ALT is normal when the ALT is less than or equal to 40 U/L, and then determining inflammation activity of the liver according to the LSM, wherein: a liver stiffness value LSM of 6.1-8.7 Kpa corresponds to mild tissue inflammatory necrosis; an LSM of 8.7-13.2 Kpa corresponds to moderate tissue inflammatory necrosis; and an LSM of 13.2 Kpa or more corresponds to severe tissue inflammatory necrosis.

2. The method according to claim 1, wherein the corresponding relationship comprises: the tissue stiffness or the parameter reflecting tissue stiffness and inflammation activity of a tissue or inflammation activity related information of a tissue corresponding to a different etiology.

3. The method according to claim 1, wherein the determining whether there is a tissue inflammation comprises:

determining whether there is clinical confirmation of abnormal tissue status;

determining whether inflammation related parameters are indicative of the presence of inflammation, when there is clinical confirmation of abnormal tissue status; and determining there is a tissue inflammation, when the inflammation related parameters indicate the presence of inflammation.

4. The method according to claim 1, wherein the determining whether there is a tissue inflammation comprises:

determining whether there is clinical confirmation of abnormal tissue status;

determining whether inflammation related parameters are indicative of the presence of inflammation, when there is clinical confirmation of abnormal tissue status;

monitoring whether there is an abnormal and sustained increase in the tissue stiffness within a first set period of time, when the inflammation related parameter indicates that inflammation is absent; and determining there is a tissue inflammation, when the abnormal and sustained increase in the tissue stiffness within the first set period of time is monitored.

5. The method according to claim 1, wherein the preset corresponding relationship comprises:

using a data of a subject to establish a Receiver Operating Characteristic curve;

using the inflammation activity of a tissue based on a pathological examination and the Receiver Operating Characteristic curve to obtain a sensitivity, a specificity, a positive predictive value and a negative predictive value of the tissue stiffness or the parameter reflecting tissue stiffness for inflammation activity of the tissue;

using the sensitivity and specificity to determine the Youden index for the inflammation activity of the tissue; and using the Youden index to determine a corresponding dividing value for the tissue stiffness or the parameter reflecting tissue stiffness.

6. A device for detecting tissue fibrosis, comprising: a memory, configured to store operation instructions; and a processor, configured to execute the operation instructions in the memory to accomplish the following operations: determining whether there is a tissue inflammation; monitoring tissue stiffness or a parameter reflecting tissue stiffness during a treatment of the tissue inflammation to determine whether the tissue inflammation has been eliminated, when there is a tissue inflammation; and obtaining a degree of tissue fibrosis or information related to the degree of tissue fibrosis according to tissue stiffness or a parameter reflecting tissue stiffness when the tissue inflammation has been eliminated or there is no tissue inflammation; obtaining of inflammation activity of a tissue or inflammation activity related information of a tissue according to the detected tissue stiffness or the detected parameter reflecting tissue stiffness when there is a tissue inflammation; wherein the obtaining of inflammation activity of a tissue or inflammation activity related information of a tissue according to the detected tissue stiffness or the detected parameter reflecting tissue stiffness comprises: obtaining the inflammation activity of a tissue or inflammation activity related information of a tissue according to a preset corresponding relationship between the tissue stiffness or the parameter reflecting tissue stiffness and the inflammation activity of a tissue or inflammation activity related information of a tissue; determining the presence of liver inflammation through alanine aminotransferase (ALT), determining the ALT is abnormal and liver inflammation is present when the ALT is greater than 40 U/L; determining the ALT is normal when the ALT is less than or equal to 40 U/L, and then determining inflammation activity of the liver according to the LSM, wherein: a liver stiffness value LSM of 6.1-8.7 Kpa corresponds to mild tissue inflammatory necrosis; an LSM of 8.7-13.2 Kpa corresponds to moderate tissue inflammatory necrosis; and an LSM of 13.2 Kpa or more corresponds to severe tissue inflammatory necrosis.

* * * * *